United States Patent [19]

Danneman et al.

[11] 4,018,887
[45] Apr. 19, 1977

[54] AMIDE-STABILIZED DRY POWDER AEROSOL ANTIPERSPIRANT COMPOSITIONS AND METHOD OF PREPARATION

[75] Inventors: Douglas L. Danneman, Forest Park; Jerry J. Yetter, Green Township, Hamilton County, both of Ohio

[73] Assignee: The Procter & Gamble Company, Cincinnati, Ohio

[22] Filed: July 27, 1971

[21] Appl. No.: 166,584

Related U.S. Application Data

[63] Continuation-in-part of Ser. No. 888,958, Dec. 29, 1969, abandoned.
[52] U.S. Cl. .................... 424/47; 424/66; 424/67; 424/68; 424/69
[51] Int. Cl.$^2$ .............. A61K 7/34; A61K 7/36; A61K 7/38
[58] Field of Search ............ 424/46, 47, 65, 66, 424/67, 68, 69

[56] References Cited

UNITED STATES PATENTS

| 2,230,082 | 1/1941 | Montenier | 424/68 |
| 2,890,987 | 6/1959 | Hilfer | 424/68 |
| 3,288,681 | 11/1966 | Goldberg et al. | 424/47 |

*Primary Examiner*—Dale R. Ore
*Attorney, Agent, or Firm*—Robert B. Aylor; Ronald L. Hemingway; George W. Allen

[57] ABSTRACT

Dry powder antiperspirant compounds are suspended in aerosol compositions by means of $C_{12}$–$C_{20}$ aliphatic alkanol amide to prevent agglomeration or packing of the antiperspirant compound in the aerosol container. Octadecyl monoethanol amide is preferred. The compositions are prepared by first dissolving and then precipitating the amide.

4 Claims, No Drawings

AMIDE-STABILIZED DRY POWDER AEROSOL ANTIPERSPIRANT COMPOSITIONS AND METHOD OF PREPARATION

CROSS-REFERENCE TO RELATED APPLICATION

This application is a continuation-in-part application of our copending application Ser. No. 888,958 filed Dec. 29, 1969, now abandoned entitled "AMIDE-STABILIZED DRY POWDER AEROSOL ANTIPERSPIRANT COMPOSITIONS AND METHOD OF PREPARATION".

BACKGROUND OF THE INVENTION

1. Field of the Invention

Antiperspirant compositions in the form of aqueous lotions, creams and sticks have been known in the art for many years. More recently aerosols under pressure have become prominent as a means of application to the skin. Among aerosols, it is especially preferred to suspend the antiperspirant compound as a dry, impalpable powder in a nonaqueous liquefied propellant form. Such a product applies the antiperspirant salt effectively to the skin and feels dry, smooth, and comfortable. Furthermore, because the antiperspirant compound is not dissolved it is not corrosive to ordinary metal aerosol cans and it is therefore not necessary to use especially lined cans or breakable glass bottles, both of which are expensive.

Typically, such a composition contains one or more metallic, acidic astringent salts as antiperspirant compound; i.e., for prespiration control. A suspending agent is employed to keep the antiperspirant compound from agglomerating or settling out and packing tightly at the bottom of the aerosol container. A carrier liquid is added so that the stream issuing from the aerosol container is a moist spray which adheres to the skin rather than a dusty cloud. Minor adjuncts are optional, such as antimicrobial compound and perfume.

PRIOR ART

Certain dry aerosol antiperspirant compositions have been disclosed in the patent literature; for example, Netherlands Pat. No. 66/13943 granted to Spitzer et al. on Apr. 4, 1968; U.S. Pat. No. 3,288,681 granted to Goldberg et al. on Nov. 29, 1966; and British Pat. No. 987,301 granted to Shulton, Inc. on Mar. 24, 1965.

SUMMARY OF THE INVENTION

It has been newly discovered that certain amides are highly effective agents for the purpose of suspending dry antiperspirant compounds in aerosol compositions which comprise:

a. From about 2% to about 12% by weight of a finely divided dry antiperspirant powder;

b. from about 0.2% to about 1% by weight of a suspending agent for the antiperspirant comprising an amide $$C_nH_{2n+1}\underset{\underset{O}{\|}}{C}-N\overset{H}{\underset{X}{\diagdown}}$$

wherein $n$ is from about 12 to about 20 and wherein X is selected from the group consisting of $-C_2H_4OH$, and $-C_3H_6OH$;

c. from about 3% to about 15% by weight of a nontoxic, non-aqueous carrier liquid of low volatility having emollient properties; and d. an anhydrous, non-toxic liquefiable propellant gas under pressure in an amount sufficient to produce an aerosol spray.

DETAILS OF THE INVENTION

Components of the Antiperspirant Formulation

Component (a).

Antiperspirant compounds suitable for use in this invention can be any of those known in the art that are insoluble in the aerosol composition as a whole. These are acidic, metallic salts, often of aluminum, zirconium, or zinc. Probably aluminum chlorhydroxide is the most widely used astringent salt though many others are also suitable: Aluminum chloride, aluminum sulfate, aluminum oxychloride, aluminum oxysulfate, zirconyl hydroxy chloride, zirconium oxychloride, zinc sulfate and zinc sulfocarbolate. In addition to these simple salts, many inorganic/organic mixtures and complexes have been suggested as antiperspirant compounds. Among these are zirconium salt/amine/amino acid complexes as taught by Siegal et al. in U.S. 3,407,254 (Oct. 22, 1968), e.g., complexes of the formula:

$$([R]_a[R']_b[ZrO][H_2O]_c)_n$$

in which:

1. R is a nucleophilic compound,
2. R' is an amino acid compound,
3. $n$ is a number of from 1 to 32 inclusive, and corresponds to the number of zirconium atoms in the molecules of the complex,
4. $a$ is a number of from 1 to 5 inclusive,
5. $b$ is a number of from 1 to 5 inclusive,
6. $c$ is a number from 0 to 4 inclusive,
7. $a+b+c$ has a value of from 2 to 6 inclusive, and
8. wherein R, R', H$_2$O and O, when present, are attached directly to Zr; zirconium salt/aluminum chlorhydroxide/glycol complexes as taught by Jones et al. in U.S. Pat. No. 3,405,153 (Oct. 8, 1968), e.g., inorganic-organic complexes having the formula:

$$n'Q.Al_2(OH)_{4-5}A_{1-3}R''_{1-4}H_2O_{1-18.5-4}$$

wherein Q is a member of the group consisting of zinc chloride, zinc iodide, zinc bromide, zinc hydroxy chloride, zinc hydroxy iodide, zinc hydroxy bromide, zirconyl chloride, and zirconyl hydroxy chloride; A is an anion selected from the group consisting of chloride, bromide and iodide; R'' is the coordinating moiety of a polyhydroxy compound having at least two carbon atoms to which are attached at least two hydroxy groups, and $n'$ is the number of moles of Q and is at least 0.05; aluminum chlorhydroxide/glycol complexes as taught by Jones et al. in U.S. Pat. No. 3,420,932 (Jan. 7, 1969), e.g., complexes having the formula:

$$Al_2(H_2O)_{y-z}(OH)_{6-n''\cdot x}(A')_{n''}(R^4)_z$$

wherein A' is selected from the class consisting of chloride, bromide, iodide, sulfate and sulfamate; R$^4$ is the coordinating moiety of a polyhydroxy compound having a carbon chain in which at least two carbon atoms link a hydroxyl group to said chain, $n''$ is a positive integer of from 1 to 4; $x$ is the valence of A', $y$ is a value of about 0.5 to 6 and is always such that $(y-z)$ does not give a negative value; and z is the number of available coordinating sites, with $n''x$ being from 2 to 4; zirconyl and aluminum halohydroxy complexes as taught by Beekman in U.S. Pat. No. 2,906,668 (Sept. 29, 1959), e.g., complexes having the formula:

in which $n'''$ is a number within the range 2-10 and the numbers of OH groups and Cl atoms are so selected, within the ranges stated, that their total will be $3n'''$; aluminum-zirconium complexes as disclosed in the copending application of Raymond E. Bolich. Jr., Ser. No. 59,690 filed July 30, 1970 entitled "ALUMINUM-ZIRCONIUM AEROSOL ANTIPERSPIRANT COMPOSITION AND PROCESS", e.g., a complex prepared by:

A. Heating an aqueous solution containing from about 1 to about 3.2 parts of aluminum chlorhydroxide to a temperature of from about 190° to about 225° F.;

B. Adding an aqueous solution containing 1 part zirconyl hydroxychloride ratewise to the aluminum chlorhydroxide solution over a period of from about 2 hours to about 5 hours while heating and agitating, the total solids content at this point being at least about 10%; and C. Heating and agitating the aluminum chlorhydroxide-zirconyl hydroxychloride mixture at a temperature of from about 190° to about 225° F. for from about ½ hour to about 5 hours until a stable complex forms.; and aluminum and zirconium hydroxychloride complexes as disclosed in the copending application of Wilmer L. Luedders et al., Ser. No. 130,833 filed Apr. 2, 1971 entitled "DRY POWDER AEROSOL ANTIPERSPIRANT COMPOSITION INCORPORATING DRY POWDER ANTIPERSPIRANT ACTIVE COMPLEX AND PROCESS FOR ITS PREPARATION", e.g., complexes prepared by:

A. Co-dissolving in water
1. one part $Al_2(OH)_{6-m}X_m$, wherein X is an anion selected from the group consisting of chloride, bromide and iodide and m is an integer from about 0.8 to about 1.2;
2. $n^4$ parts ZrY wherein Y is an anion selected from the group consisting of —O(OH)Cl and $OCl_2$, and where $n^4$ has a value of from about 0.16 to about 1.2;
3. $p$ parts neutral amino acid selected from the group consisting of glycine, dl-tryptophane, dl-$\beta$-phenylalanine, dl-valine, dl-methionine and $\beta$-alanine, and where $p$ has a value of from about 0.06 to about 0.53;

B. Co-drying the resultant mixture at a temperature of from about 100° to about 230° F. to a moisture level of from about 0.5% to about 15% by weight; and C. Comminuting the resultant dried inorganic-organic antiperspirant complex into the form of an impalpable powder.

These patents and applications are incorporated herein by reference.

The choice of antiperspirant compound is limited only by normal factors well-known to those skilled in the art. Commercial availability is widespread. The abovementioned aluminum salts are preferred, and aluminum chlorhydroxide and the complexes disclosed in the applications of Luedders et al. and Bolich are especially preferred.

As mentioned supra, the antiperspirant compound is dispersed in finely-divided, powder form. The particle size of this compound must be small enough to remain suspended in the composition within the aerosol container, to pass through the valve without clogging, to disperse on the skin to provide adequate coverage, and to react rapidly enough with the moisture of the skin and air to convert the antiperspirant compound in dry powder form into the ionic state which is needed for effectiveness in suppressing perspiration.

Particle sizes smaller than about 100 microns are suitable for the practice of this invention, with particles averaging from about 10 microns to about 25 microns being preferred. The amount of antiperspirant compound is also governed by normal factors. Between about 2% and about 12% by weight of the composition is suitable for perspiration control for an aerosol burst of the duration the consumer is wont to use. Below about 2% the antiperspirant effectiveness drops off. Above about 12% is not practical because the antiperspirant effectiveness does not increase commensurate with additional quantities used; and in addition viscosity of the product increases so that handling is more difficult and atomization is less satisfactory. Preferred usage is from about 2.5% to about 6%.

Component (b).

The newly-discovered suspending agent of this invention is an amide. In particular it is a saturated aliphatic monoalkylol amide with from about 12 to about 20 carbon atoms in the fatty chain and 2 or 3 carbon atoms in the alkylol chain. Preferred is a saturated aliphatic monoalkylol amide with 16 or 18 carbon atoms in the fatty chain and 2 carbon atoms in the alkylol chain. Especially preferred is octadecyl monoethanol amide. In general the effective amides of the instant invention are solid, not liquid, at room temperature.

The amides defined above unexpectedly keep the aforementioned finely-divided powdered antiperspirant compound suspended in the composition as a whole. The antiperspirant does not settle to the bottom of the aerosol container and pack tightly into a compact solid mass nor does it clump or coagulate into large agglomerates that cannot be dispersed and dispensed with substantial uniformity.

From about 0.2% to about 1% of these amides by weight of the composition are suitable for the practice of the instant invention. At least 0.2% is required to accomplish the suspending function of this component. With amides that are relatively low in chain length, i.e., n is 12 or 14, solubility in the composition is increased and amounts somewhat higher than 0.2% are required. More than 1% is not required to perform the suspending function. In addition, excessive amounts of this component increase the viscosity of the composition which adversely affects ease of handling and atomization. Preferred usage of the amides of the instant invention is from about 0.3% to about 0.8% with from about 0.4% to about 0.7% by weight of the composition being especially preferred.

Alkylol amides used in the practice of the instant invention can be made by reacting fatty acids with monoethanol amine or monopropanol amine. Commercial sources of these amides in purities of 80 to 95% are commonplace.

Component (c).

A carrier liquid of low volatility is used in the instant invention so that the stream issuing from the aerosol container is a moist spray rather than a gritty, dusty cloud. This imparts a cosmetic feeling to the skin when applied thereto and reduces the likelihood of breathing the otherwise dry powder. The carrier liquid also aids efficacy by keeping the antiperspirant compound in contact with the skin so that it does not flake off or wash off. Thus the carrier liquid is needed for practical use of the instant invention though it is not required per se for purposes of preparing a dry powder antiperspirant composition in stable form.

Any of the carrier liquids that are known in the art are suitable for the compositions of the instant invention. Examples are: Lanolin and fractions of lanolin such as those prepared by the teachings of U.S. Pat. No. 2,758,125, e.g., Lantrol, either as themselves or as their derivatives such as acetylated lanolin alcohols, e.g., Acetol prepared and refined according to U.S. Pat. No. 3,272,851, ethoxylated lanolin alcohols ethoxylated with from 1 to about 40 moles of ethylene oxide, hydrogenated lanolin alcohols such as Hydroxyol, lanolin fatty acids esterified with lower ($C_1$–$C_4$) fatty alcohols such as Isopropyl Lanolate; silicone oils such as polysiloxanes having the formula $[-R_2^5Si\,O-]_n$ where $R^5$ can be $C_1$–$C_4$ alkyl, phenyl, carboxyalkyl, etc., and the polysiloxane can have a viscosity at 25° C. of from about 5 to about 2,000 centistokes; Fluid AP; polyalkylene glycols which can contain a fatty acid or fatty alcohol group containing from about 2 to about 20 carbon atoms such as polyethylene glycol monolaurate and butoxy-polyoxyethylene oxypropylene glycols [The Ucon 50 HB series; Trade Mark — Union Carbide]; fatty alcohols containing from about 12 to about 18 carbon atoms such as lauryl, myristyl, hexadecyl, octadecyl, and oleyl alcohols; fatty acid esters of aliphatic alcohols where said esters contain from about 12 to about 26 carbon atoms such as ethyl laurate, isopropyl myristate, isopropyl palmitate, isopropyl behenate, decyl acetate, behenyl butyrate, hexadecyl acetate, decyl decanoate, methyl oleate, lauryl laurate, and oleyl acetate; aliphatic hydrocarbons such as mineral oil having a specific gravity at 60° F. of from about 0.8 to about 0.9 and aliphatic hydrocarbons containing from about 12 to about 26 carbon atoms such as tetradecane, hexadecane, nonane, tetracosane, etc.; esters containing multiple ester groups such as those disclosed in the copending application of Wilmer L. Luedders, Ser. No. 59,694 filed July 30, 1970 entitled "IMPROVED EMOLLIENTS FOR PARTICULATE ALUMINUM", i.e., a multiple ester organic compound of from about 12 to about 16 carbon atoms having a ratio of ester groups to carbon atoms of from about 0.125 to about 0.214 and having a solubility in water of from about 0.0005% to about 0.1% at 30° C., examples being di-n-octyl-n-decyl phthalate, di-n-octyl phthalate, di-n-hexyl phthalate, di-n-butyl phthalate, diethyl sebacate, diisopropyl adipate, and ethyl ethylcarbomethyl phthalate [ortho $C_2H_5OOC$-$\phi$-$COOCH_2COOC_2H_5$].

Still other operable carrier liquids are even more hydrophilic than these esters. Among them are polyethylene glycol monolaurate and butoxy-polyoxyethylene oxypropylene glycols [the Uncon 50 HB series; Trade Mark — Union Carbide].

Among these various carrier liquids, carboxylic esters having from about 12 to about 26 carbon atoms are preferred. As described supra, they can be either aliphatic or aromatic and can contain either one ester group or multiple ester groups. Especially preferred are di-n-butyl phthalate, diethyl sebacate, diisopropyl adipate, and ethyl ethylcarbomethyl phthalate.

Any of the carrier liquids described supra can be used in amounts from about 3% to about 15%. Below about 3% the carrier liquid is insufficient to form a moist spray and the spray is, therefore, undesirably dusty and gritty and does not adhere well to the skin. Above about 15% the composition deposited upon the skin feels undesirably oily and greasy. Amounts of carrier liquid from about 6% to about 10% are preferred.

Component (d).

The propellant gas of the instant invention can be any liquefiable gas conventionally used for aerosol containers. Examples of materials that are suitable for use as propallants are trichlorofluoromethane, dichlorodifluoromethane, dichlorotetrafluoroethane, monochlorodifluoromethane, trichloritrifluoroethane, propane, butane, 1,1-difluoroethane, 1,1-difluoro-1-chloroethane, dichloromonofluoromethane, methylene chloride, and isobutane, used singly or admixed. Trichlorofluoromethane, dichlorodifluoromethane, dichlorotetrafluoroethane, and isobutane, used singly or admixed, are preferred.

The amount of the propellant gas is governed by normal factors as well known in the aerosol art. It is satisfactory to consider the propellant as constituting the balance of the composition of the instant invention that is not accounted for by the other components as detailed herein. The preferred limits of propellant are therefore from about 70.7% to about 93.9%. Especially preferred limits are from about 80% to about 92%.

Component (e).

Minor ingredients commonly used in the art are optional. Perfumes are one such ingredient, used in amounts up to about 0.8% by weight. Another is an antimicrobial compound, such as hexachlorophene, trichlorocarbanilide, trifluoromethyl carbanilide, and tribromosalicylanilide. Antimicrobials are used in amounts up to about 0.5% by weight to inhibit bacterial action upon perspiration and thereby reduce the resultant odors.

Processing

The essential elements of the process of the instant invention are i. From a solution by dissolving component (b) in component (c) or component (d) or a mixture thereof;
ii. Mix component (a) into said solution; and
iii. Precipitate component (b).

Step (i) can be accomplished by dissolving the amide, component (b), at relatively high temperature [preferably ca. 160°–190° F.] in the carrier liquid, component (c). Alternatively, it can be done by dissolving the amide at a lower temperature [preferably ca. 130°–160° F.] in a propellant having an atomic ratio of chlorine to fluorine from about 2 to about 3, in which the amide is relatively soluble, as for example in $CCl_3F$ or $CCl_2FCCl_2F$. A mixture of carrier liquid and propellant of this type is also suitable as a solvent for component (b) and, in this case, the lower temperatures mentioned above are preferred.

Step (ii) can be done concurrently with step (i) or separately if desired.

Step (iii) can be accomplished by cooling to about 30°–80° F. Alternatively it can be done by adding a propellant having an atomic ratio of chlorine to fluorine from about 0.5 to about 1 in which the amide is relatively insoluble, as for example $CCl_2F_2$ or $CHClF_2$. In ordinary practice cooling accompanies addition of such a propellant because the propellant is stored cool, but this is not essential to the process.

It is preferred to carry out cooling in a scraped-wall vessel to avoid the formation of agglomerative chunks.

The following three paragraphs disclose in somewhat more detail how these processing steps can be carried out in preparing small laboratory batches and larger batches, respectively. In the Examples a variety of specific procedures are given as they were used to prepare specific formulations. Although the details of these preparations vary greatly, they all accomplish the essential elements (1), (2), and (3) as set forth supra. Those skilled in the art will recognize other possible minor modifications thereof.

To prepare stabilized compositions of the instant invention on a small scale (e.g., 500 grams) the suspending agent [component (b)] and the carrier liquid [component (c)] are heated and mixed together. The antiperspirant compound [component (a)] is added with moderate agitation under conditions such that the resultant temperature is about 160° to about 190° F. This mixture is allowed to cool to about 100° F. and minor ingredients [component (e)] are added with moderate agitation. The composition at this point, hereinafter called a "concentrate", is allowed to stand until it reaches room temperature or below. It is then charged into an aerosol container and low pressure propellant [e.g., trichlorofluoromethane] is added. The container is sealed and heated to 140° F. for two minutes; shaken to assure homogeneity; allowed to cool to about 120° F.; and pressure-filled with higher pressure propellant [e.g., dichlorodifluoromethane]. It will be recognized by those skilled in the art that slightly modified filling procedures will be used when the propellant consists entirely of low pressure or entirely of high pressure propellant.

The process described supra can be adapted to commercial practice if desired. Each step can be performed successively in the individual aerosol container on the production line. Certain components can be put into each can, heat and agitation can be applied, and the remainder of the components can be added. If propellant is among the first group of components, it will be necessary to attach the valve at this point and add the remainder of the components by pressure fill. In this case it is often convenient to use a relatively high boiling propellant like trichlorofluoromethane in this first group of components.

However, it can be advantageous for large scale work to prepare a batch of concentrate in a single vessel, omitting the propellant in whole or in part. The concentrate is then charged into individual aerosol containers, propellant added by under-the-cup fill, and the containers sealed. In the Examples that follow, several variations of this method are described.

Testing of the Compositions

Compositions of the instant invention were tested for stability of the suspension by filling glass aerosol containers, storing at temperatures from 140° to 20° F., for periods ranging from one month to 12 months, respectively, and examining for separation and ability to redisperse. Color and odor were observed. Compositions were similarly stored at various temperatures for various times in commercial aerosol cans and examined for can corrosion, lining deterioration, absence of clogging in the valve, and satisfactory spray rates and patterns therefrom. Human subjects judged whether the deposit of the spray upon their skin was aesthetically pleasing. The compositions were also examined for their mildness to the skin, eyes, nose and throat, and their absence of sensitization.

In the Examples to follow, the properties supra will be referred to as "general physical properties".

Effectiveness of perspiration control was determined on human subjects as percent reduction in sweat for a treated, as compared with an untreated, axilla.

EXAMPLE I

Sixteen hundred grams of isopropyl myristate, the carrier liquid, and 120 grams of coconut monoethanol amide, the suspending agent, were weighed into a vessel and heated to about 160° F., whereupon the mixture was completely liquified. Seven hundred grams of aluminum chlorhydroxide (17% moisture powder), the antiperspirant compound, was added and the resulting concentrate was mixed for 5 minutes. As it cooled to about 120° F. the sides of the vessel were scraped occasionally by hand. The concentrate was allowed to stand for about 5 hours during which time it formed a solid gel. This gel was whipped with an agitator until it becomes fluid and 20 grams of trichlorocarbanilide and 60 grams perfume was added and mixed in. Portions of the batch were transferred to aerosol containers which were then sealed and pressure-filled with propellant to yield the following composition:

| | |
|---|---|
| Aluminum chlorohydroxide | 3.5% |
| Coconut monoethanolamide | 0.6 |
| Isopropyl myristate | 8.0 |
| Trichlorocarbanilide | 0.1 |
| Perfume | 0.3 |
| Propellant-$CCl_3F$:$CCl_2F_2$::60/40 (weight ratio) | 87.5 |
| | 100.0% |

Antiperspirant properties were good and general physical properties as defined in the preceding section, were good.

The same process is used to prepare compositions identical to the foregoing except that different kinds of propellants are used as shown in the following list and table. In each case the general physical properties and the antiperspirant effectiveness of the composition when applied to the skin are substantially the same as that discussed above.

1,1-difluoroethane,
1-chloro-1,1-difluoroethane,
dichloromonofluoromethane,
methylene chloride,
methyl chloroform,
vinyl fluoride, and
vinylidene fluoride, as 100% of the propellant.

| Propellant | % By Weight on a Propellant Basis [100% propellant is equivalent to 87.5% of the composition] | | | | | | | | | | | | |
|---|---|---|---|---|---|---|---|---|---|---|---|---|---|
| | a | b | c | d | e | f | g | h | i | j | k | l | m |
| Trichlorofluoromethane | 100 | | | | | | | | 40 | | | 60 | 30 |
| Dichlorodifluoromethane | | 100 | | | | | | | 30 | 40 | 30 | | |
| Dichlorotetrafluoroethane | | | 100 | | | | | | | 60 | 40 | | |
| Monochlorodifluoromethane | | | | 100 | | | | | | | | 40 | |
| Trichlorotrifluoroethane | | | | | 100 | | | | | | | | 30 |
| Propane | | | | | | 100 | | | 30 | | | | |
| Butane | | | | | | | 100 | | | | 30 | | |
| Isobutane | | | | | | | | 100 | | | | | 40 |
| Total | 100 | 100 | 100 | 100 | 100 | 100 | 100 | 100 | 100 | 100 | 100 | 100 | 100 |

EXAMPLE II

Forty-eight pounds of dibutyl phthalate and 3.6 lb. of octadecyl monoethanol amide were weighted into a drum and heated to about 160° F., whereupon the mixture was completely liquefied. Twenty-one pounds of aluminum chlorhydroxide was added and the resulting concentrate was mixed for 5 minutes. The mixture was cooled to about 120° F. with agitation and allowed to stand overnight. Five and seven-tenths pounds perfume and 0.6 lb. trichlorocarbanilide was added and mixed in. The batch was packed into aerosol containers by adding 21 gm. of the above concentrate; sealing; and pressure filling with 143 gm. of a 60/40 mixture of $CCl_3F/CCl_2F_2$. The composition was:

| Component | % By Weight of the Composition | | | | | | | |
|---|---|---|---|---|---|---|---|---|
| | a | b | c | d | e | f | g | h |
| Trichlorocarbanilide | 0 | 0 | 0 | 0 | 0.5 | 0 | 0.2 | 0 |
| Hexachlorophene | 0 | 0.1 | 0 | 0 | 0 | 0.1 | 0 | 0 |
| Trifluoromethylcarbanilide | 0 | 0 | 0.1 | 0 | 0 | 0.1 | 0 | 0 |
| Tribromosalicylanilide | 0 | 0 | 0 | 0.1 | 0 | 0.2 | 0 | 0 |
| Perfume | 0 | 0.1 | 0 | 0.1 | 0.5 | 0.5 | 0.8 | 0.3 | the change in these minor ingredients, with the type of propellant remaining unchanged. Also in each case the general physical properties and the antiperspirant effectiveness of the composition when applied to the skin are substantially the same as that discussed above.

EXAMPLE III

A full factorial statistically designed experiment was conducted, with 1000 gram batches of each composition infra. The concentrates containing all components except propellant were prepared by the method of Example I. Portions of the batch were transferred to aerosol containers; $CCl_3F$ was added; the containers were sealed and placed in a hot tank at about 140° F for about 7 minutes; $CCl_2F_2$ was added by pressure fill.

| | a | b | c | d | e | f | g | h |
|---|---|---|---|---|---|---|---|---|
| Aluminum chlorhydroxide | 3.5% | 3.5% | 3.5% | 3.5% | 3.5% | 3.5% | 3.5% | 3.5% |
| Octadecyl monoethanol amide | 0.75 | 0.25 | 0.75 | 0.25 | 0.75 | 0.25 | 0.75 | 0.25 |
| Dibutyl phthalate | 11.3 | 11.3 | 4.7 | 4.7 | 11.3 | 11.3 | 4.7 | 4.7 |
| Trichlorocarbanilide | 0.1 | 0.1 | 0.1 | 0.1 | 0.1 | 0.1 | 0.1 | 0.1 |
| Perfume | 0.45 | 0.45 | 0.45 | 0.45 | 0.45 | 0.45 | 0.45 | 0.45 |
| Propellant - $CCl_3F$ | 50.2 | 50.7 | 56.8 | 57.3 | 62.6 | 63.1 | 69.2 | 69.7 |
| - $CCl_2F_2$ | 33.7 | 33.7 | 33.7 | 33.7 | 21.3 | 21.3 | 21.3 | 21.3 |
| | 100.00 | 100.00 | 100.00 | 100.00 | 100.00 | 100.00 | 100.00 | 100.00 |

| | |
|---|---|
| Aluminum chlorhydroxide | 3.5% |
| Stearyl monoethanol amide | 0.6 |
| Dibutyl phthalate | 8.0 |
| Trichlorocarbanilide | 0.1 |
| Perfume | 0.4 |
| Propellant-$CCl_3F$:$CCl_2F_2$::60/40 (weight ratio) | 87.4 |
| | 100.0% |

Antiperspirant properties were good and general physical properties were good.

The same process is used to prepare compositions identical to the above except that different kinds and amounts of antimicrobial are used and different amounts of perfume are used. In each case the propellant is adjusted slightly in amount to compensate for Antiperspirant properties were good and general physical properties were good.

The same process is used to prepare compositions identical to that of Example III c. except that the octadecyl monoethanol amide is replaced by 0.3% eicosyl monoethanol amide, 0.2% hexadecyl monoethanol amide, 1.0% tetradecyl monoisopropanol amide, and 0.8% octadecyl mono-n-propanol amide. In each case the usage of propellant $CCl_3F$ is adjusted correspondingly. Anti-perspirant effectiveness is good and general physical properties are good.

EXAMPLE IV

Forty grams of diisobutyl adipate and 3 gm. octadecyl monoethanol amide were heated to 190° F and mixed; then cooled to 180° F. and 17.5 grams of aluminum chlorhydroxide and 0.5 gm. trichlorocarbanilide were added and mixed while natural cooling was allowed to occur. Perfume in the amount of 2.2 gm. was added when the mix reached 150° F. The batch was chilled for 20–30 minutes and remixed; then added to aerosol containers to which 262.1 gm. CCl$_3$F was added and the valves applied. After a hot tank test 174.7 gm. CCl$_2$F$_2$ was added by pressure fill. The composition had good general physical properties and good antiperspirant effectiveness.

The same process was used to prepare compositions identical to the foregoing except that diethyl sebacate, dibutyl phthalate, ethyl ethylcarbomethyl phthalate, and isopropyl myristate, respectively, were substituted for the diisobutyl adipate. The general physical properties were substantially the same as the foregoing. The compositions were effective antiperspirants.

The same process is used to prepare compositions identical to the foregoing except that the diisobutyl adipate is replaced by other carrier liquids: di-n-octyl-n-decyl phthalate, di-n-octyl phthalate, di-n-hexyl phthalate, isopropyl palmitate, mineral oil, tetradecane, lauryl alcohol, hexadecyl alcohol, oleyl alcohol, dimethyl polysiloxane having a specific viscosity at 25° C. of 350 centistokes, lanolin, Acetol, lanolin alcohols ethoxylated with about 5 moles of ethylene oxide, Hydroxyol, isopropyl ester of lanolin fatty acids, Fluid AP, polyethylene glycol (2.5 moles) monolaurate, butoxypolyoxyethylene (5.0) oxypropylene (5.0) glycol, myristyl alcohol, octadecyl alcohol, 3-ethyldodecyl alcohol, isopropyl myristate, isopropyl behenate, decyl acetate, ethyl laurate, behenyl acetate, hexadecyl acetate, decyl decanoate, methyl oleate, lauryl laurate, oleyl acetate, hexadecane, nonane, tetracosane, and mineral oil having a specific viscosity of about 0.865. General physical properties and antiperspirant effectiveness are substantially the same as those of Example IV.

EXAMPLE V

Forty-two grams of aluminum chlorhydroxide, 3.6 gm. octadecyl monoethanol amide, 48 gm. dibutyl phthalate, and 0.6 gm. trichlorocarbanilide were weighed into a vessel, heated to about 180° F and allowed to cool to 100° F. Two and four-tenths grams of perfume was added and the batch mixed again. Portions of the concentrate were transferred to aerosol containers which were then sealed and filled with propellant by the method of Example III to yield the following composition:

| | |
|---|---|
| aluminum chlorhydroxide | 7.0% |
| octadecyl monoethanolamide | 0.6 |
| dibutyl phthalate | 8.0 |
| trichlorocarbanilide | 0.1 |
| perfume | 0.4 |
| propellant - CCl$_3$F:CCl$_2$F$_2$::60/40 | 83.9 |
| (weight ratio) | 100.0% |

Antiperspirant properties were good and general physical properties were good.

The same process is used to prepare compositions identical to the above except that the aluminum chlorhydroxide is replaced by other antiperspirant salts: aluminum chloride, aluminum sulfate, aluminum oxychloride, aluminum oxysulfate, zirconyl hydroxychloride, zirconium oxychloride, zinc sulfate, zinc sulfocarbolate, and complexes of zirconium salt/amine/amino acid, zirconium salt/aluminum hydroxychloride/glycol, aluminum hydroxychloride/glycol, and zirconyl-/aluminum hydroxychlorides where all said salts and said complexes are dried and comminuted to form particles of substantially the same size as the aluminum chlorhydroxide, said complexes being those disclosed in the specific examples of U.S. Pat. Nos. 3,407,254; 3,405,153; 3,420,932; and 2,906,668, and the applications of Wilmer L. Luedders et al., Ser. No. 130,833 filed Apr. 2, 1971, and Raymond E. Bolich, Jr., Ser. No. 59,690 filed July 30, 1970, referred to hereinbefore. Other particulate antiperspirant materials will also be suspended by the amides of this invention. Antiperspirant properties are exhibited and general physical properties are substantially the same as those of the above.

The same process is used to prepare compositions identical to those of Example V except that 24 grams of dibutyl phthalate are replaced by 24 grams of isopropyl myristate, making thereby a mixed carrier liquid. Antiperspirant properties and general physical properties are substantially the same as those of the above.

Additional properties similar to the above were prepared which contained as antiperspirant 3.5% aluminum chlorhydroxide substituted for 7.0% aluminum chlorhydroxide. The mixed propellant was reduced from 83.9% to 80.4%. General physical properties were good. Antiperspirant performance for the 7.0% aluminum chlorhydroxide preparation was numerically better than for the 3.5% aluminum chlorhydroxide preparation, but the difference was not statistically significant at the 95% confidence level.

Other compositions similar to the above are prepared which contain as antiperspirant 2% and 12% aluminum chlorhydroxide respectively. In each case the quantity of mixed propellant is adjusted correspondingly. Antiperspirant effectiveness and general physical properties are good.

When in the above examples the following complexes are substituted for the aluminum chlorhydroxide, substantially equivalent results are obtained in that the compositions are good antiperspirant compositions and the antiperspirant powder is suspended.

Complex I is prepared by the following procedure:

15.0 parts by weight of aluminum hydroxychloride (50% aqueous solution) was added to a beaker. Glycine was then added in an amount of 2.0 parts by weight and dissolved with the aid of a suitable mixer. Zirconyl hydroxychloride (33⅓% aqueous solution) was then added and mixed in an amount of 13.8 parts by weight. The combined components were then mixed until co-dissolved. The co-dissolved solution was then dried in an oven at a temperature of about 120° C. until a moisture content of 3% was attained. The dried solution now in a solid state was then placed into a ball mill and milled for about four hours which resulted in a fine powder. The powder was then passed through a 325 mesh screen to obtain a uniform size product.

Complex II is prepared as follows:

155 grams of a solution (50% nominal concentration) of aluminum chlorhydroxide (ACH) in water is heated in a suitable container to raise the temperature to 190° F. (The solution is agitated during the heating, utilizing suitable agitating means.) About ⅓ of 138 grams of a solution (33⅓ nominal concentration) of zirconyl hydroxychloride (ZHC) in water is then added in bulk to the ACH solution; and the remainder of the ZHC solution is added to the ACH solution in small portions over a period of 3 hours, the heating and agitation being continued during this period, and for about 3 hours after all the ZHC has been added. The heating and agitation is then stopped and the resulting aqueous complex (41% nominal concentration) is allowed to cool. The aqueous solution is subsequently dried in an oven at a temperature of 140° C. until a moisture content of about 5% is attained. The dried solution, now in a solid state, is then placed into a ball mill and milled for about 4 hours, giving a fine powder. The powder is then passed through a 325 mesh screen to obtain a uniform size product.

What is claimed is:

1. A powder aerosol antiperspirant composition comprising:
    A. from about 2% to about 12% by weight of a finely divided dry antiperspirant powder selected from the group consisting of aluminum chlorhydroxide, and complexes of aluminum chlorhydroxide and zirconyl hydroxychloride;
    B. from about 0.2% to about 1% by weight of a suspending agent for the antiperspirant comprising an amide having the formula

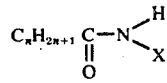

wherein $n$ is from about 12 to about 20 and wherein X is selected from the group consisting of —$C_2H_4OH$, and —$C_3H_6OH$;
    C. from about 3% to about 15% by weight of a non-toxic, non-aqueous carrier liquid of low volatility having emollient properties selected from the group consisting of lanolin, polysiloxanes of the formula (—$R_2^5SiO$—)$_n$ wherein $R^5$ is $C_1$-$C_4$ alkyl or phenyl and wherein said polysiloxanes have a viscosity at 25° C. of from 5 to about 2,000 centistokes, polyalkylene glycols containing a fatty acid or fatty alcohol group containing from about 2 to about 20 carbon atoms, fatty alcohols containing from about 12 to about 18 carbon atoms, fatty acid esters of aliphatic alcohols wherein said esters contain from about 12 to about 26 carbon atoms, mineral oil having a specific gravity of from about 0.8 to about 0.9 at 60° F., aliphatic hydrocarbons containing from about 12 to about 26 carbon atoms, multiple ester organic compounds of from about 12 to about 16 carbon atoms having a ratio of ester groups to carbon atoms of from about 0.125 to about 0.214 and having a solubility in water of from about 0.0005% to about 0.1% at 30° C., and mixtures thereof; and
    D. from about 70.7% to about 93.9% by weight of an anhydrous, non-toxic liquefiable propellant gas, under pressure.

2. The composition of claim 1 wherein component (B) comprises from about 0.3% to about 0.8% by weight and $n$ is 16 or 18; and component (C) comprises from about 6% to about 10% by weight of a carboxylic ester having from about 12 to about 26 carbon atoms.

3. The composition of claim 2 wherein component (B) comprises from about 0.4% to about 0.7% by weight of octadecyl monoethanolamide; and component (C) comprises from about 6% to about 10% by weight of di-n-butyl phthalate, diethyl sebacate, diisopropyl adipate, or ethyl ethylcarbomethyl phthalate.

4. The composition of claim 3 wherein present are components (A), (B), (C) and (D), and in addition:
    E. from 0% to about 0.5% by weight of trichlorocarbanilide, hexachlorophene, trifluoromethyl carbanilide, or tribromosalicylanilide; and
    F. from 0% to about 0.8% by weight of perfume.

* * * * *